(12) United States Patent
Plew et al.

(10) Patent No.: US 7,207,274 B1
(45) Date of Patent: Apr. 24, 2007

(54) STICKY POLYMER LETHAL AGENT TRACER

(75) Inventors: Tara Y. Plew, Orlando, FL (US); Leslie D. Kramer, Longwood, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 11/186,199

(22) Filed: Jul. 20, 2005

Related U.S. Application Data (60) Provisional application No. 60/589,498, filed on Jul. 20, 2004.

(51) Int. Cl.
*F42B 5/24* (2006.01)
(52) U.S. Cl. ............................ 102/501; 102/513
(58) Field of Classification Search ............... 102/501, 102/502, 513
See application file for complete search history.

(56) References Cited

U.S. PATENT DOCUMENTS 4,614,157 A * 9/1986 Grelle et al. ................ 102/466
6,512,478 B1 * 1/2003 Chien .................... 342/357.09
6,650,283 B2 11/2003 Brydges et al.

OTHER PUBLICATIONS

Dow Corning, http://www.dowcorning.com/content/etronics/etronicsseal/default.asp☐☐Date verified using www.waybackmachine.org: Jun. 2, 2002.*

* cited by examiner

*Primary Examiner*—Michael J. Carone
*Assistant Examiner*—Gabriel J. Klein
(74) *Attorney, Agent, or Firm*—Jeffrey D. Myers; Timothy D. Stanley; Peacock Myers, P.C.

(57) ABSTRACT

A monitoring device and method comprising providing a projectile comprising a sticky medium, one or more sensors embedded therein, and a data transmitter receiving input from said one or more sensors, and firing the projectile at a target to which the medium will attach.

4 Claims, 2 Drawing Sheets

STICKY POLYMER LETHAL AGENT TRACER

CROSS-REFERENCE TO RELATED APPLICATIONS

This application claims priority to and the benefit of the filing of U.S. Provisional Patent Application Ser. No. 60/589,498, entitled "Sticky Polymer Lethal Agent Tracer", filed on Jul. 20, 2004, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention (Technical Field):

The present invention relates to a method and device for remotely emplacing and monitoring sensing explosives, chemical warfare agents, and/or controlled substances and/or emplacing a CCD camera for locating potential security threats.

2. Description of Related Art

At present, it is difficult to remotely detect explosives or drugs, such as on a small naval vessel approaching one's own vessel. Bomb/drug-sniffing dogs are, of course, known in the art, but must operate from a very close proximity to the threat.

The present invention provides the ability to remotely detect threats, an ability not heretofore available. The projectile of the invention with chemical sensors and a radio transmitter can be shot at and deployed on potential threats such as approaching ships, motor vehicles, trash heaps, and like potential locations of threats. The invention can also be used for personnel/hostage detection by use of CCD cameras and/or MEMS microphones.

BRIEF SUMMARY OF THE INVENTION

The present invention is of a monitoring device and method comprising: providing a projectile comprising a sticky medium, one or more sensors embedded therein, and a data transmitter receiving input from said one or more sensors, and firing the projectile at a target to which the medium will attach. In the preferred embodiment, the one or more sensors comprise one or more MEMS sensors, CCD cameras, and/or GPS receivers. The sensors can include any combination of explosive, chemical, radiation, biological, and acoustical sensors. The sticky medium is preferably a sticky polymeric medium, most preferably a two-part dielectric gel polymer. The sticky medium can be placed in a housing, most preferably comprising polyethylene terephthalate polyester and/or conforming to the shape of a gun barrel of a gun configured to fire the projectile.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention provides soldiers, policemen, and like security personnel with a way of remotely sensing explosives, chemical warfare agents, or other threats, and/or employing a Charge-Coupled Device (CCD) camera for locating potential threats, thus reducing the threat to lives. The invention can also have a Global Positioning System (GPS) receiver chip integrated into the projectile of the invention to allow geolocation simultaneous with the sensor detection event.

Figure 1:
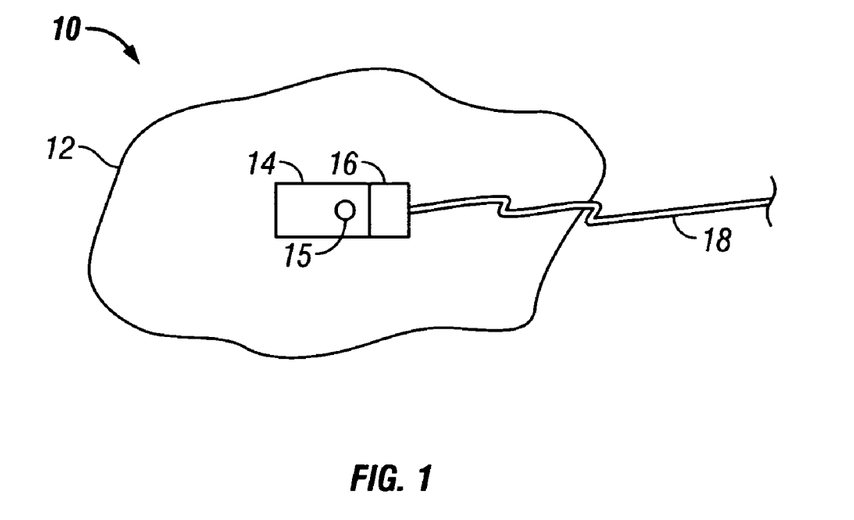
FIG. 1 is a diagram of a projectile according to the invention without solid housing.
Figure 2:
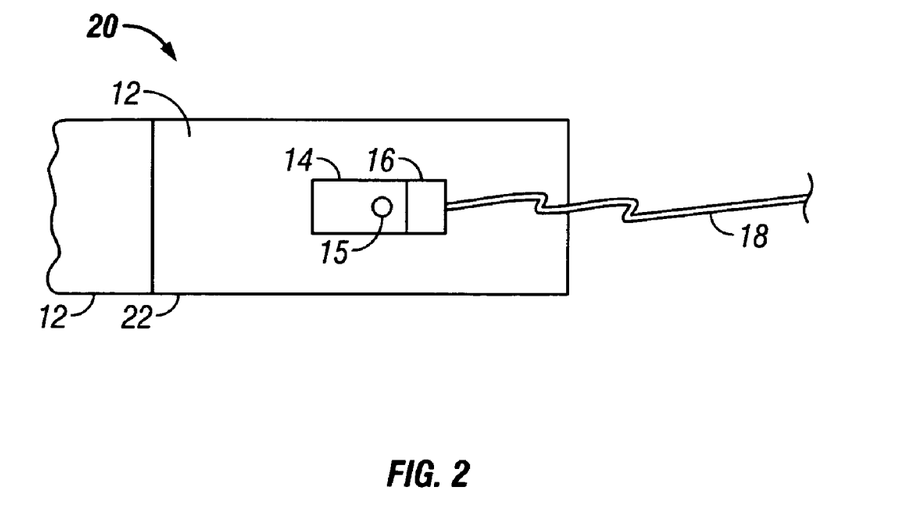
FIG. 2 is a diagram of a projectile according to the invention with solid housing.

In the preferred embodiment, one embeds a Micro Electro Mechanical Systems (MEMS)-based sensor (explosive, chemical, radiation, biological, and/or acoustical) and Radio Frequency (RF) link into a sticky polymeric medium, thus forming a projectile (FIG. 1), or else the systems can be embedded in a housing at the front of which is a glob of sticky polymeric material (FIG. 2). The projectile can then be fired to tag a suspected threat area (e.g., car, trash pile, bridge, building, etc.) using a standard paintball gun ($CO_2$ powered) or modified standard issue rifle. The sensor transmits data back to the deployer at a safe range from the threat area. To tag the exact location of the suspected threat area, the projectile can contain a GPS receiver. While one embodiment of the projectile has a range of 240 feet using a paintball gun, standard methods for surviving high-"G" loads are applicable to much larger ranges and velocities. Other communications means can be employed in place of an RF link, including communication via optical tag. Items other than sensors can be used, including delayed reaction munitions, smoke generators, and the like (such devices could be set to ignite if an only if sensors detect one of a set of conditions, such as presence of TNT).

There is at present no remote, virtually undetectable, non-lethal, easily-used, quick detection system is available to provide warning to a soldier (or other security personnel) or to provide the ability to monitor hostage location/enemy locations (or other event locations).

Referring to FIG. 1, the projectile 10 of the invention comprises sticky material 12, electronic systems 14 (e.g., MEMS explosive, chemical, radiation, biological, and/or acoustical sensor(s), RFID tag, CCD camera, and/or GPS circuitry), power supply 15, transmitter 16, and antenna 18. Referring to FIG. 2, the projectile 20 of the invention adds a housing 22 containing most of the sticky material 12 and the embedded systems.

The preferred sticky material has a consistency similar to that of human mucous. The most preferred material is a two-part dielectric gel polymer, such as available from Dow Corning as product 3-4130. When a housing is used, the preferred housing is made of a copolyester of polyethylene such as PETg, such as that commercially known as Vivak™.

The preferred alternative deployment mechanisms are: paintball gun, beanbag gun, blow gun, slingshot, and potato gun, each of which is next discussed.

Paintball guns, also called paintball markers, are common and easy to obtain. The variety of paintball guns means there is a larger selection to match needs. Paintball gun bore sizes vary from 0.680 to 0.700 in. The bore size limits the size of the MEMS projectile, which reduces the size of the devices and the amount of dampening material inside the projectile. Paintball guns can fire paintballs at speeds of 200 to 300 feet per second (fps). The speed varies with the amount of pressure from the tank or cartridge, so changing the projectile speed means only varying the pressure.

Beanbag guns fire a bag with lead shot pellets and are meant as a non-lethal weapon for law enforcement. They come in two forms:

Fire-arm delivery: The beanbags come rolled in ammunition shells and are fired with shotgun, gas gun, or M203 launcher. The shells come in three sizes: 12 gauge, 37 mm, and 40 mm. The 12 gauge (0.73 in.) shells are fired with the shotgun, and the 37 and 40 mm shells are fired with gas gun or M203 launcher. Twelve gauge shells have a two inch square bag filled with 40 grams of #9 lead. One hundred gram, 5 by 1.5 in., bags are used for the 37 and 40 mm shells. The shells are fired at 300 feet per second and have a range of 30 to 100 ft. These bag ammunitions are for law enforcement use only.

Pneu-gun ballistic baton delivery: Similar to the fire-arm delivery, but uses a $CO_2$ cartridge as the power to launch the shot bag. The gun fires the bags at a speed of 300 fps. The $CO_2$ power allows for use by non law enforcement individuals.

Blow guns are long tubes that can fire darts or paintballs. They vary in size from 36 to 60 in. in length and have a bore size of 0.40 and 0.50 in. The shafts are made from aluminum, wood, or plastic and come as one or two pieces. Projectiles can reach speeds of up to 350 fps in the muzzle and have a range of 250 ft.

Slingshots fire projectiles with a rubber band and can launch them up to 600 ft at speeds up to 300 fps. Slingshots can fire a variety of different size objects from 0.25 to 0.50 in. Accuracy depends upon the ability of the user.

Potato guns are homemade devices that are usually made from PVC piping and other common items. The guns can fire an assortment of objects, but received their name from successfully launching potatoes up to 300 ft. There are two types of potato guns:

Hairspray gun: Uses hairspray, Static Guard, or 91 percent rubbing alcohol as the combustion fuel. The fuel is sprayed into a chamber for several seconds then closed immediately. The fuel is ignited by either a lantern lighter or other spark producing item. The combustion is loud and the process for launching is inexact. The gun is home-built so safety is a concern. They are illegal in many states.

Compressed air gun: The gun setup is similar to that of the hairspray gun, but compressed air is used to launch the projectile instead of combustion. The launch chamber is filled with air until a pressure of around 100 psi is reached. Then a valve is opened, either by hand or by electronic switch, and the projectile is launched. The air can be pumped into the chamber by bicycle or electric pump. Ranges of 600 ft have been recorded.

The compressed air gun is safer than the hairspray gun because there is no explosion launching the projectile. There is still danger in putting too much air pressure in the chamber. Both guns can be built at various sizes, but typical guns have had a barrel bore size of 1.5 to 2 in. and lengths of 3 to 10 ft.

Out of the five gun types considered, the paintball gun fit the best with expected needs. Paintball guns are more expensive than the blow gun and slingshot, but they are more accurate and predictable. The beanbag gun is for law enforcement only and is more expensive than the paintball gun. The potato gun is dangerous and illegal, but the large bore size is ideal for the dampening needed for the MEMS device.

The casing which surrounds the adhesive polymer and the MEMS device will have a large influence on how well the projectile sticks to the target. A few different methods are described below.

A gelatin casing would be similar to a paintball casing. The casing must be soft enough to keep the projectile from being lethal but stiff enough to take the acceleration force when shot out of the gun. When the casing impacts the target, the debris may remain between the polymer and the surface.

A mesh casing can surround the polymer and MEMS device. When the projectile hits the target, the polymer will squeeze through the mesh onto the target. This method decreases the debris between the polymer and surface which will give a larger surface area for the contact of the polymer and surface.

One can combine the above two methods. The outer casing would be a mesh casing but within that casing the polymer and the MEMS device will be encased within a solid sphere. When the projectile hits the target the polymer squeezes out of the mesh casing and the MEMS device is protected from the impact force by the solid casing surrounding it.

The chemical composition of the polymer and casing are also important. The two must be able to stay in contact with each other without degrading the important properties of either one. For example, one could use a styrene-butadiene block copolymer placed into a paintball casing, but the paintball casing becomes too soft and does not shatter on impact.

MEMS is a term used to categorize many different devices fabricated on the micron scale. It includes sensors, actuators, and instruments which are usually fabricated using integrated circuit technology. MEMS technology integrates micro-electrical components with micromechanical components into an all inclusive system. MEMS are an extremely diverse technology that will be used in many different applications. Testing of the present invention included use of a MEMS accelerometer as a sensor for acceleration.

There is a huge variety of chemical sensors. Two main types of chemical sensors include the Metal Oxide sensors and the Polymer-Carbon sensors. The Metal Oxide sensors can detect fixed gases such as $O_2$, $Cl_2$, $H_2$, NO, etc. The Polymer-Carbon sensors (PCS) cannot detect these gases but can detect a large variety of chemicals such as pure solvents, complex mixtures, and natural products. PCS work by absorbing some of the sample into the polymer and this will change the conductance through the sensor which is measured to decide what chemicals are in the sample. The response of a PCS can be from less than two seconds to fifteen seconds depending on the chemical being detected. A company making PCS for detecting specific chemicals is Cyrano Sciences.

Most acoustic sensors are piezoelectric, which means that they transform mechanical energy into electrical energy and vice versa. Acoustic sensors transform sound into an electrical output. Different types of acoustic sensors include Flexural Plate Wave Devices, Shear-Horizontal Surface Acoustic Wave Devices, Love Wave Devices, and Thickness Shear Mode Resonators. Acoustic sensors usually have a devise which senses the sound and propagates which then creates a voltage drop. Acoustic sensors are widely available since they are used for a variety of reasons. Some manufacturers of acoustic sensors are Militronics, Miltec, and Endevco.

The present invention is intended to deliver any combination of sensors now known or developed in the future, as needed for specific operations.

The preferred power supply is a battery. Due to size limitations there typically will only be one battery to power both the MEMS sensor and the transmitter. It is best to choose low power consumption devices for both the sensor and transmitter. Different types of batteries include lithium batteries, micro alkaline batteries, and silver oxide batteries.

Lithium batteries are unique in that they are available in both primary (nonrechargeable) and secondary (rechargeable) styles. They provide a high energy storage capacity and long operational life. Lithium batteries consist of a lithium anode, which is an organic electrolyte that conducts the current, and a cathode. Lithium ions are driven from the cathode into the anode and back again when charge is removed. The lithium battery can be used to power devices or backup devices. When used to backup devices they serve as a long term power source so that memory components can retain necessary information. Since they are made from the lightest of all metals, lithium, they are light in weight making them good for powering portable devices.

Thin film batteries are usually rechargeable lithium and lithium-ion batteries that are flat and very thin, resembling a piece of paper. These flexible batteries are much thinner, lighter, safer, less expensive and have higher energy density than typical lithium batteries. They are usually made of Lithium or Lithium-ion. They do not contain toxic materials as do NiCad batteries. They do not leak. They have thicknesses ranging from 2 to 20 microns and surface areas on the order of 1 cm2. These batteries also have longer cycle life, energy density, and shelf life than normal lithium batteries.

Micro alkaline batteries are commonly found in electronic calculators, electronic clocks, electronic watches, and many other devices. The alkaline battery uses manganese dioxide ($MnO_2$) as its positive active material and zinc (Zn) as its negative active material. Potassium hydroxide (KOH) is used as an electrolyte. They provide good cost-performance because they use low-cost manganese dioxide. Some common secondary alkaline batteries and examples include:

Nickel-cadmium batteries (NiCd): NiCd batteries are the most commonly found and used rechargeable batteries. They are very dependable but are not very environmentally friendly.

Nickel-Metal hydride (NiMH): NiMH batteries provide 10–25% greater capacity than NiCd and are more environmentally friendly.

Nickel-Zinc batteries (NiZn): NiZn are characterized by a high specific energy and power capability. They are commonly used for electric vehicle applications, such as small vans and passenger cars.

Silver plays an important role in the high performance battery market today. Silver's conductivity provides high energy with minimum weight and volume. The only real disadvantage is its relative short life and high cost. Used to power small electronic products it is highly used in military projects as well as satellites. The most common form of silver oxide battery is the small silver oxide-zinc battery; also know as "button cells". These batteries are used for a variety of different consumer products, including watches, calculators, cameras, and hearing aids. The trade off between cost and absolute reliability is not an option for many of the applications for which these batteries are intended. Many of the applications require very high energy densities while maintaining a light load. Silver oxide batteries satisfy these conditions. Astronauts use silver oxide batteries in there space suits for space walk life support systems and power tools. Other silver systems include coupling silver with cadmium, magnesium, and hydrogen. These different systems have much narrower applications.

When examining the different properties and characteristics of each type of battery, one can make some conclusions. The lithium and silver oxide batteries have a higher cost in comparison with the alkaline batteries. However, both lithium and silver oxide batteries are more efficient in providing power. Lithium ion is made from the lightest of all metals and in essence is the lightest of all the batteries, and it also has the smallest size. When comparing alkaline and silver oxide one can conclude that alkaline batteries have better cost-performance and superior leakage resistance. Comparing lithium and alkaline one can say that even though more costly, lithium lasts longer, is lighter, and is able to function at a greater range of temperatures.

As to propulsion of the projectile, the $CO_2$ used in paintball and other similar systems is compressed down into liquid form. Liquid $CO_2$ is extremely cold and draws ambient heat when converting to gas. The converting may cause a frosted tank or jammed gun. If liquid got into the gun non-metal components may be damaged. Listed below are possible solutions to keep liquid $CO_2$ out of the gun.

Expansion chamber: A segregated tube with multiple chambers slows the flow of liquid $CO_2$ and provides an area to absorb ambient heat to convert into a gas state. Since it cannot control the pressure of the $CO_2$ gas, fluctuating pressures resulting in varying projectile exit velocities may occur.

Regulator: A $CO_2$ tolerant regulator provides control of the fluctuations associated with the propellant thus allowing consistent pressure. It is effective in preventing $CO_2$ from entering the gun. A regulator provides the best control of liquid $CO_2$.

Anti-siphon: A small metal tube attached to the inside of the pin valve on the tank. The tube can bend into a position that ensures only gaseous $CO_2$ is drawn from the tank. While the cheapest solution, it does not prevent pressure fluctuations. Since the device must be installed directly onto the $CO_2$ tank, professional installation is recommended. Improperly installed anti-siphon tubes may draw straight liquid.

The pressure of $CO_2$ gas changes with temperature. Liquid $CO_2$ absorbs ambient heat to convert to gas, so temperature directly affects the rate of change. The higher the ambient temperature, the greater the pressure can be. The rate of fire may also decrease the pressure due to the rapid conversion from liquid to gaseous $CO_2$ and the ability of the tank to transfer the heat surrounding it to the liquid.

Nitrogen propulsion and HPA propulsion are interchangeable for paintball and other similar systems. Air and compressed air both refer to HPA systems. $N_2$ and air may be stored in the same tanks and work almost identically under given situations.

HPA tanks come with a pre-installed, either adjustable or fixed regulator. If using a fixed regulator, the preference is a high-pressure output-opposed to a low-pressure output. An adjustable regulator allows the exiting pressure to be controlled. Installing a regulator on the gun—in addition to the pre-installed tank one—permits fine tuning of the gas pressure.

HPA and nitrogen systems permit a lighter (compared to steel), fiber wrapped tank. A thin shelled aluminum tank wrapped in carbon or Kevlar fibers that are embedded in resin add strength to the tank. Protective covers that prevent scratches or gouges are recommended. A hydro test should be performed every three to five years, depending on the tank.

Contemporary designs of projectiles often involve an explosive such as gunpowder as a propellant. The modern bullet cartridge comprises of a bullet, bullet casing, propellant (gunpowder), and a primer. The basic idea involves a firing pin striking the primer and causing it to explode. The propellant ignites, driving the bullet down the gun barrel.

$CO_2$ is the standard entry level propulsion in paintball and other similar systems, but it may damage O-rings and other parts of the gun from its freezing temperature in liquid form. HPA does not damage the gun since it is continually in a gas form, thus not reaching freezing temperatures. Gunpowder, while useful in projecting hard substances such as metal, may contribute to the failure of the MEMS device and other components of the project. Unregulated $CO_2$ fluctuates in pressure greatly and can cause velocity spikes. HPA does not fluctuate and will give consistent pressure thus helping with accuracy and range. HPA tanks are considerably more expensive than $CO_2$ tanks and HPA tank refills are more expensive than $CO_2$ refills.

The link between the MEMS sensor and a receiving unit consists of three different stages. The electronic components inside the projectile preferably comprise the sensor(s), power supply, transmitter, and antenna. The basic information flow of the system is as follows. The sensor will provide a response to some changing environmental condition producing an analog signal at its output, this signal will then be fed to the transmitter where it will be introduced into some kind of modulation scheme, than this modulated signal will be amplified (still in the transmitter) to a power level sufficient enough for propagation through the last stage, the antenna. The next stage in our communications link is the actual channel which consists of the polymer material used for dampening and adhesion and after escaping this environment it will encounter air. One must take into account the change between the different regions and assess the consequences of signal attenuation. The final stage in the communications link is the receiving end. This stage consists of the receiver and signal processing components. The receiver will need an antenna, input amplifier, and a decoder/demodulator.

A very important aspect of the invention is data integrity and the ability to transmit data from the MEMS sensor to a receiver at some distance away. There are many different factors to consider when deciding on a specific transmitter to use. Listed below are a few of the criteria to be considered:

Size: The size of the transmitter must be chosen to fit inside the 0.68 inch diameter paintball (or other deployment device) along with the MEMS sensor, battery, and antenna.

Frequency: The Federal Communications Commission (FCC) is in charge of regulating communications in the United States. A viable frequency range for amateur use is at 2.4 GHz. This is also a common frequency used in commercial radio frequency components. The dilemma in choosing this frequency is again related to size restrictions. At 2.4 GHz the antenna needs to be at least 1.23 inches, determined by $\lambda/4$. Since the diameter of the paintball is only 0.68 inches, this is a problem. Taking this into account, note that increasing the frequency would allow for a smaller antenna size. At a frequency of 10 GHz or higher one then has enough room for the antenna.

Power Consumption: Finding a transmitter with the lowest power consumption is necessary for an extended battery life. Due to size limitations usually only one power supply will be available to both the sensor and transmitter. Ensuring that both devices have low power consumption will allow an increased shelf life of the product.

Modulation Type: Choosing what type of modulation would depend on the availability taking into consideration complexity. Different modulation types include the following: Analog (Amplitude Modulation (AM) or Frequency Modulation (FM)); and Digital (Amplitude Shift Keying (ASK) or Frequency Shift Keying (FSK)).

The modulation type chosen will determine two characteristics. First, it will determine the bandwidth of the transmitted signal and the receiver bandwidth. Also, the translation between signal-to-noise ratio and the resulting bit error rate will be determined. Determining which modulation to use will depend on factors such as:

Complexity: Different modulation techniques have different levels of complexity in terms of circuit design. The more complex circuit design needs a larger implementation area.

Environmental Factors: Different environmental factors include noise, interference from buildings and other obstacles are better dealt with by different modulation techniques.

Cost: Different modulation techniques are more costly than others. For example amplitude demodulation is inexpensive compared to frequency demodulation. Also implementation of a digital system compared to an analog system has a difference in cost. Digital system will require more components such as an analog to digital converter, external clock, and microcontroller. It is up to the designer to select an implementation method that will maximize performance, yet minimize cost.

Additional circuit components needed for transmission include the following:

Crystal Oscillator: Many of the circuit diagrams that must be implemented in conjunction with the transmitter show the presence of a crystal oscillator. The crystal controlled oscillator provides a stable frequency for oscillation Antenna: The antenna is a key part of transmission system. An antenna's radiation pattern and gain are perhaps the two characteristics that most affect system coverage and performance.

The receivers' job is to extract the source of information from the received modulated signal. The two main classes of receivers are the tuned radio-frequency (TRF) receiver and the superheterodyne receiver. Most receivers are the latter. The superheterodyne receiving technique consists of either down-converting or up-converting the input signal to some convenient frequency band, called the intermediate frequency (IF) band, where the information is extracted by a demodulation process. The receiver must be compatible with the transmitter. Therefore it must have the same frequency and be able to demodulate the signal modulation. It must have a high sensitivity, meaning it must be able to distinguish between the signal and unwanted noise. It will then amplify this signal before demodulating to recover the data.

The key components of the receiver are the following:
Antenna: The receiving antenna acts somewhat like a catcher's mitt and intercepts the transmitting antennas power in an effective area.
Power gain input: The signal received by the receiver will be amplified. This is needed due to the attenuation effects of the environment.
Demodulation: Demodulation is the process of recovering the message from the received signal. The transmitter and receiver must be of the same modulation scheme for demodulation to take place. This will take place inside the transmitter.
Signal Processing: After the signal is received one needs to interpret the data.

Some adhesives are based on a solvent-evaporation system to create physical bonds (Elmer's Glue®). Others must be heated to the molten state, the necessary physical bonds occur upon cooling to the solid state (hot glue). Still others are based on an epoxy-hardener system where the two components are combined and allowed to cure (JB Weld®). The curing process allows the mixture to crosslink thus hardening. No matter the mechanism of physical bond formation, initial viscosity needs to be low to allow the material to flow and spread over the surface, filling crevices and voids on a micro- and macroscopic level. Pressure-sensitive adhesives (PSAs) are unlike other types of adhesives because they exhibit 'quick stick' behavior allowing repeated bonding and debonding (Post-it™).

Pressure-sensitive adhesives (PSAs) exhibit fast adhesion to a substrate. This occurs because the use-temperature (room temperature) is sufficiently high above the glass-transition temperature (Tg) to allow viscous flow.

For PSAs, tack is defined as the property whereby the adhesive will adhere tenaciously to any surface it comes into contact under light pressure. The strength of the bond is greater under increasing pressure [1]. Tack is a maximum between 40 and 70° C. above Tg—meaning the Tg of all PSAs should fall between −15 and −45° C. However, most polymers are not sufficiently tacky enough on their own. Therefore, other substances are added to increase the tackiness of the material called tackifiers. Besides increasing the tackiness of a polymer, the modulus decreases as well. The application of pressure on the material causes it to flow, and filling crevices and voids on a micro- and macro-scopic level. A good surface area contact is necessary for firm adhesion.

Three main types of PSAs exist-polyacrylates, block copolymers, and natural rubbers.
Polyacrylates: Depending on the structure of the acrylic acid ester (i.e., acrylate) monomer, polyacrylates are intrinsically sensitive to pressure without the additional dissolved components such as tackifiers. (However, addition of tackifiers is an option for those polyacrylates that do not exhibit the intrinsic properties necessary for a good PSA.) This property of polyacrylates is advantageous because the absence of dissolved low molecular weight species prevents diffusion to the bond surface. Concentration gradients and compositional variations at the substrate-adhesive interface can be deleterious to the physical/mechanical bonds formed over time. Typically one wants a homogenous contact between the substrate and the adhesive. The purpose of the polymer chains is to diffuse and spread over the substrate surface creating interlocking bonds. The purpose of the admixtures is secondary—only to aid in this process. The diffusion of the dissolved components to the surface can only interfere with the bonds present. (Note: This diffusion occurs over an extended period, so it only becomes significant for applications on the order of months to years.)
Moreover, the carbon backbone of polyacrylates are saturated, meaning all carbon atoms composing the polymer backbone are sp3 hybridized-no double bonds. Double bonds absorb light. However, when the light contains sufficient energy the double bonds break forming radicals that propagate through the polymer causing chain scission events at other double bonds. Therefore, photodegradation is less likely to occur with saturated polymeric backbones.
Block copolymers: Block copolymers consist of two different monomers connected in grouped segments, as opposed to random connections. The monomer components of the polymer backbone phase segregate into clusters of similar chemical composition and structure.
The requirements for a good pressure-sensitive block-copolymer are the Tgs with respect to the environmental temperature. One segment or block of the polymer must have a Tg well above use conditions; the other segment must have a Tg well below use conditions. The high Tg components are termed hard while the low Tg components are termed soft. At operational temperatures sufficiently below the glass-transition temperature, materials are rigid and glass-like. By extension, the aggregation of like block segments with a high Tg are hard as well. There hard, rigid agglomerations are sites of physical crosslinks. They restrict the motion of the soft, flexible segments.
Further subdivision of the block copolymer category yields the saturated and unsaturated classes. The terms saturated and unsaturated refer to the hybridization of the flexible block in the polymer backbone. Unsaturated block copolymer can undergo further crosslinking with the addition of sulfur through the double bonds.
Natural rubbers: Natural rubber, derived from rubber trees, is a polymer called cis-polyisoprene. It is the most common PSA. However, raw cis-polyisoprene alone is not sufficiently tacky enough to be used as a PSA, so tackifiers are added. Natural rubber can be crosslinked through the isoprene double bonds with sulfur creating a disulfide bridge between adjacent polymer chains. This polymer must undergo additional processing to achieve the pressure-sensitive status. For example, the raw polymer is masticated to reduce its molecular weight. Based on the viscoelastic theory of adhesion, molecular weight distribution (MWD) is important when predicting adhesion. For example, a narrow MWD for a polymer would not allow chains to flow because of the high associated viscosity. A broad MWD for a polymer would have sufficient numbers of short chains that could act as plasticizers to the viscosity of the material and diffuse through the interface region from the bulk polymer to the surface (more so than the longer, entangled chain fractions) making an intimate contact with the surface.

A polymer shell and dyed oil comprise the components of a paintball. Processed collagen is the paintball shell. Collagen is a triple helix of fibers. The fibers are long polymer chains called polypeptides or proteins made from condensation reactions with amino acids. It consists of the nine essential amino acids except for tryptophan.

Collagen is a main component of connective tissue and bone. A hydrolytic process to form gelatin degrades the molecular weight (MW) of collagen. Derived from gelatin, paintball shells encase the dye. The components of the dye include a low viscosity, low MW oil (e.g., vegetable oil), and food coloring.

Unmodified paintballs left in an air-conditioned, laboratory environment for the same time duration showed no shell softening. Since the liquid inside the gelatin shell is a nonpolar hydrocarbon, one may assume gelatin is soluble in polar solvents like water but not soluble in nonpolar solvents like vegetable oil. This assumption holds when considering the microstructure of gelatin and the adage "like dissolves like." The nitrogen and oxygen atoms in the polymer backbone and in the side groups of gelatin can undergo hydrogen bonding with water.

The consequence of atmospheric water adsorption on the mechanical properties of the gelatin shell is the critical velocity needed for fracture. Brittle materials like dehydrated gelatin compared to ductile materials like atmospheric-softened gelatin absorb less energy before fracture. Therefore, for a given distance from the muzzle end to the target, a greater velocity (i.e. a greater kinetic energy) is needed to break the shell and expose the PSA so that it may adhere to a surface. If the final projectile design calls for a PSA encased within a gelatin shell, then any long-term storage may result in a softened shell. Gun design and gas pressure restrict maximum projectile velocity limiting effective range—the maximum distance a projectile casing will break exposing sufficient adhesive material to make contact with a surface. A softened shell will limit the effective range further.

Commercially available PSAs in bulk form (as opposed to tape form) exist primarily as toys for children. One such toy, SPLAT!®, is a block copolymer of styrene and butadiene. The attractiveness of poly(styrene-block-butadiene-block-styrene) or SBS to children and this project resides in the adhesive nature. The material is moderately tacky to the touch. However, the impact when thrown against a surface causes adhesion.

The styrene-butadiene copolymer is moist, soft, and elastic. In uniaxial-tensile tests at low strain rates, the material exhibits high extension before ductile failure; in uniaxial-tensile tests at high strain rates, the material exhibits low extension before brittle failure. However, when removed from its airtight container and left for 24 h in an air-conditioned, laboratory environment, the material becomes dry, hard, and brittle. One possible explanation is volatile-solvent evaporation: the additives that decrease modulus and increase tack diffused to the polymer surface and evaporated. Moreover, noticeable adhesion between the gelatin shell and the copolymer occurred.

The consequence of volatile-solvent evaporation on the mechanical properties of the styrene-butadiene copolymer is the quality of the adhesive bond. Pressure-sensitive adhesives need to flow readily in order to fill surface flaws and make a strong interlock. A dried, embrittled polymer lacks this necessary requisite. Undoubtedly, in ballistic tests, the dried SBS would not adhere to a surface. Furthermore, if the final projectile design calls for the copolymer encased within a gelatin shell (not completely airtight), then long-term storage and solvent evaporation may exacerbate shell softening.

A testfire was the next step to determine the viability of SBS as a potential PSA for this project, despite the shortcomings. Fabrication of the projectile consisted of packing two gelatin-shell halves with the copolymer. The projectile was front-end loaded about 4 in. down the muzzle of a Brass Eagle® pump-action paintball gun. Fired at a painted (semigloss) concrete wall, the muzzle end-to-target distance was about 5 ft. The results of the testfire showed that the SBS projectile did not adhere to the target surface. Inspection of the projectile revealed that substantial shell fragments were imbedded within the copolymer. These fragments might have impeded the minimum surface area necessary to allow adhesive bond formation.

Another PSA is polyvinylidene fluoride (PVDF). Typical uses for PVDF range from piezoelectric films to chemical resistant tank linings. The material is highly tacky to the touch. Once touched, the material is often difficult to remove from the hands.

Unlike SBS, PVDF retains its mechanical properties in an air-conditioned, laboratory environment over a 24-h period. This could mean the additives are stable at standard temperature (25° C.) and pressure (1 atm) or that no additives are present. This eliminates the problem concerning storage and shelf life as seen with SBS. Moreover, no noticeable adhesion between the gelatin shell and PVDF occurred. One possible explanation for the observed nonstick behavior is that oil residue from the dye interfered with the adhesive bond.

As before, a testfire was the next step to determine viability of PVDF as a potential PSA for this project. Fabrication was similar to that described for SBS except for the addition of a circuit: a voltage gain op-amp. The circuit was tested before the testfire confirming proper function. The same test parameters for the SBS projectile were used. The results of the testfire showed that the PVDF projectile adhered to the target surface. Subsequent testing of the circuit confirmed proper function—no change in voltage gain compared to the pre-testfire check. One possible explanation for the successful testfire is the lack of shell fragments to impede contact. Observations indicate that before impact one shell half fell away from the PVDF-circuit mass exposing more of the polymer to the target surface. It is thought that the nonstick oil layer aided in this process. This serendipitous finding suggested a new mode of projectile design to explore.

When the projectile hits the desired object, it will be at a high velocity and to ensure that the electronics are not damaged it's paramount to find an effective device to damp the force. Damping possibilities are as follows:

Springs would damp the force of impact. The kinetic energy of the projectile would be dissipated and turned into potential energy. For a spherical or oblong shaped projectile the MEMS device, the transmitter and the battery would be placed inside a shell and springs along with a sticky polymer would be placed outside that shell but within the outer shell. For the jack shell structure the springs would be placed inside of the shell. For the open cylinder shell structure the springs would be placed inside the adhesive substance, which would be sticking out of both ends of the open cylinder. The electronics would be placed in the location most effective for damping the force.

A polymer can be used to dampen the force of impact, such as the sticky polymer itself. For a spherical, oblong, or jack shaped shell structure a polymer would be placed around and in contact with the electronics inside the projectile. For an open cylinder shell structure the polymer would be sticking outside of both ends of the open cylinder with the electronics placed inside of the polymer. The electronics would be placed in the location most effective for damping the force.

Honeycomb can be used to damp the force of impact. Honeycomb is lightweight as well as strong in compression. For the spherical, oblong and jack shaped shell structure the design would be similar to the spring dampening system with the MEMS device, transmitter, and battery inside a small shell with honeycomb and an adhesive substance outside of that, but still inside the projectile. For the open cylinder shell structure the honeycomb would be placed inside of the adhesive substance which would be outside of both ends of the cylinder. The electronics would be placed in the location most effective for damping the force.

Jacks can also be used to damp the force of impact. For the spherical, oblong and jack shaped shell structure the electronics would be encapsulated along with jacks. For the open cylinder shell structure the jacks would be placed inside of the adhesive substance which would be outside of both ends of the cylinder. The electronics would be placed in the location most effective for damping the force.

The polymer damping system is considered most efficient, most cost effective, and the easiest to implement.

INDUSTRIAL APPLICABILITY

The invention is further illustrated by the following non-limiting example.

EXAMPLE 1

Tests were performed for a Sticky Polymer Optical Tag (SPOT) according to the invention, employing a plastic projectile fabricated from a standard polymer casing of Polyethylene Terephthalate Polyester (PETg) filled with a dielectric gel polymer adhesive. By selecting a sticky polymer to adhere to the target, the designator provides a non-lethal and non-destructive solution for tagging a target. With careful selection of both the polymer and casing materials, the necessary environmental conditions can be satisfied.

The small, non-lethal, non-destructive projectile was designed to be shot from a standard paintball gun with a maximum range of approximately 100 meters and carrying a 17.2 mm projectile. The data reported was performed with this style of projectile. The simplicity of the SPOT casing and adherence mechanism makes it an ideal candidate for manufacturing and for use as an optical designator.

The casing for SPOT is a standard copolyester of polyethylene known as PETg. Commercially known as Vivak™, it is one of the toughest transparent materials known today as evidenced by its 50 MPa tensile strength. Copolyesters also exhibit extreme impact strength, even at low temperatures. The working temperatures of PETg range from −40° C. to 65° C., and it exhibits a 0.2% absorption of moisture when immersed at −23° C. for 24 hours.

These properties allow PETg to be fabricated using a plethora of techniques such as die cutting, shearing, cold bending, stapling, riveting, sawing, drilling, milling and routing. PETg also has excellent thermoforming properties, allowing them to be molded into shapes such as hollow tubes at low temperatures, without the need for predrying. PETg allows ~90% transmittance of the visible spectrum even after thermoforming.

By using ballistic design and fabrication techniques, the casing can be constructed such that the leading edge explodes, or "petals", outward, thus allowing the polymer to adhere to the targeted surface.

The adhesive used to adhere the optical designator to the target is a specially cured, two-part dielectric gel polymer. This gel is typically used for sealing and protecting various electronic devices, especially those with delicate components. The gel polymer, made commercially by Dow Corning, is extremely soft, giving it excellent thermal/mechanical shock and vibration damping. The gel also has a wide working temperature range, varying from −45° C. to 150° C. The flexible cure schedule is the key ingredient to varying the tackiness of the gel by controlling the amount of cross-linking that occurs. This two-part gel is compatible with automated dispensing equipment, which makes it easily manufacturable and cost-effective.

To form the adhesive gel, parts A and B are mixed in equal parts inside the mold and projectile casing to the desired amount. The mixture is then cured at 40° C. for 6 hours to achieve the desired tackiness.

Based upon the material properties, experiments were conducted to test the adhesion versus temperature and varying environmental conditions for further evaluation of the gel for use in SPOT.

Figure 3:
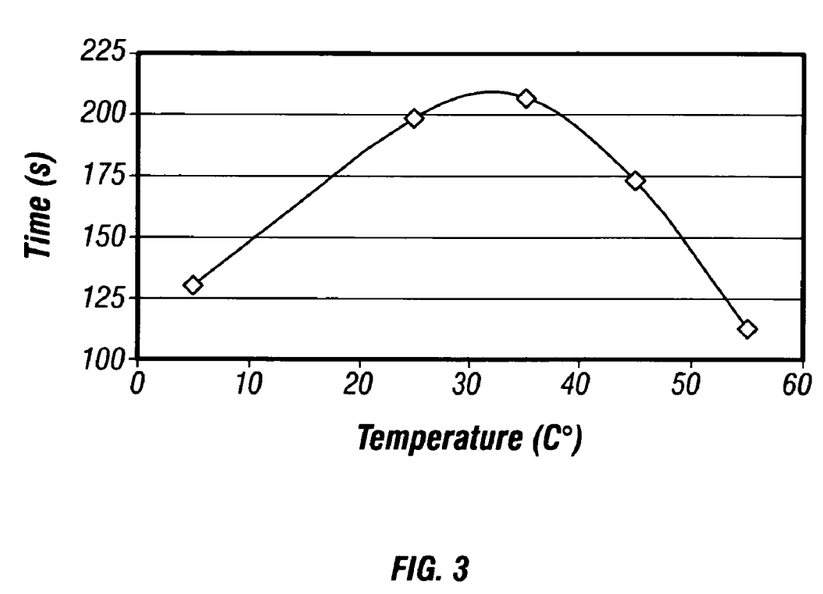
FIG. 3 is a graph of temperature versus adhesion time in minutes for the preferred sticky polymer of the invention.

For the adhesion versus temperature experiments, a 16.3 g weight was attached to the polymer. This in turn was encased in a cylindrical 17.2 mm PETg projectile. The assembly was then attached to the underside of a smooth aluminum surface. This experiment was performed in triplicate. The aluminum was then heated to temperatures ranging from 5° C. to 55° C., and the time for each polymer to release from the surface was recorded. The average values are graphically reported below.

Graphical data suggest the optimal adhesion temperature is around 35° C. The adhesion times continually decrease after 35° C. This may imply that at these elevated temperatures the polymer is heated enough to begin a micro-scale thermoforming process to increase the cross-linking of the polymer molecules, thus reducing the tackiness of the gel. This theory needs to be further examined and tested before being accepted as the explanation for reduced adhesion times at elevated temperatures.

The ability of the polymer to adhere to a wet or sandy surface condition was also tested. As before, a 16.3 g weight was attached to the polymer. This was encased in a cylindrical 17.2 mm PETg projectile, and the assembly was then attached to the underside of a sand-coated aluminum surface. Like the earlier study this experiment was performed in triplicate. The temperature was held at a constant 30° C. and the time it took for the polymer to release from the sample surface was recorded and is presented below:

| Polymer Conditions Test Data at 30° C. | | | | |
| --- | --- | --- | --- | --- |
| Condition | Trial 1 (s) | Trial 2 (s) | Trial 3 (s) | Avg. Adhesion Time (s) |
| Wet | 403 | 413 | 490 | 435 |
| Sandy | 130 | 215 | 250 | 198 |

The polymer adheres better under moist conditions than the sandy conditions. However, this can be remedied by designing a small mechanical latch system into the tip of the projectile, embedded into the adhesive polymer to catch in sandy conditions, but to shear away during other conditions.

With successful adaptation, SPOT is an ideal candidate for a optical designator. It provides a simple, cost-effective, easily manufactured, non-lethal and non-destructive solution for tagging various target surfaces in multiple environments.

The preceding example can be repeated with similar success by substituting the generically or specifically described reactants and/or operating conditions of this invention for those used in the preceding example.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A monitoring device comprising a projectile comprising a sticky polymeric medium comprising a two-part dielectric gel polymer, one or more MEMS sensors embedded therein, a data transmitter receiving input from said one or more sensors, and a housing for said sticky polymeric medium, said housing comprising polyethylene terephthalate polyester.

2. The monitoring device of claim 1 wherein said housing conforms to a shape of a gun barrel of a gun configured to deliver said projectile.

3. A monitoring method comprising the steps of providing a projectile comprising a sticky polymeric medium comprising a two-part dielectric gel polymer, one or more MEMS sensors embedded therein, a data transmitter receiving input from said one or more sensors, and a housing for said sticky polymeric medium, said housing comprising polyethylene terephthalate polyester, and firing the projectile at a target to which the medium will attach.

4. The monitoring method of claim 3 wherein the housing conforms to a shape of a gun barrel of a gun configured to fire the projectile.

* * * * *